United States Patent [19]

Ura et al.

[11] 3,988,368

[45] Oct. 26, 1976

[54] PROCESS FOR PRODUCING PHENYLPHOSPHONOTHIOIC DICHLORIDE

[75] Inventors: Yasukazu Ura; Hideki Takamatsu, both of Funabashi, Japan

[73] Assignee: Nissan Chemical Industries, Ltd., Tokyo, Japan

[22] Filed: June 12, 1975

[21] Appl. No.: 586,392

[30] Foreign Application Priority Data

June 22, 1974 Japan .............................. 49-71616

[52] U.S. Cl. ..................... 260/543 P; 260/606.5 P
[51] Int. Cl.² .......................................... C07F 9/42
[58] Field of Search ................... 260/543 P, 606.5 P

[56] References Cited
UNITED STATES PATENTS

| | | | |
|---|---|---|---|
| 2,662,917 | 12/1953 | Jensen | 260/543 P |
| 2,870,204 | 1/1959 | Lecher et al. | 260/543 P |
| 2,993,929 | 7/1961 | Rattenburg | 260/543 P |
| 3,359,312 | 12/1967 | Buchner et al. | 260/543 P |
| 3,457,307 | 7/1969 | Groenweghe | 260/543 P |
| 3,504,025 | 3/1970 | Maier | 260/543 P |
| 3,790,629 | 2/1974 | Uhing et al. | 260/543 P |
| 3,879,454 | 4/1975 | Hinkamp et al. | 260/543 P |
| 3,897,491 | 7/1975 | Toy | 260/543 P |

*Primary Examiner*—Norman Morgenstern
*Attorney, Agent, or Firm*—Oblon, Fisher, Spivak, McClelland & Maier

[57] ABSTRACT

In a process for producing phenylphosphonothioic dichloride by reacting benzene with thiophosphoryl trichloride, an improvement is characterized in that the reaction is conducted in the presence of a catalyst selected from the group consisting of Al, $AlCl_3$, a combination of $AlCl_3$, $P_2S_5$ and $PCl_3$, a combination of $AlCl_3$ and $P_2S_5$, and a combination of $AlCl_3$ and $PCl_3$, under the self-generated pressure of hydrogen chloride gas.

9 Claims, No Drawings

PROCESS FOR PRODUCING PHENYLPHOSPHONOTHIOIC DICHLORIDE

BACKGROUND OF THE INVENTION

1. Field of the Invention

The present invention relates to a process for producing phenyl phosphonothioic dichloride (hereinafter referred to as PPTC). More particularly, it relates to a process for producing PPTC by reacting benzene with thiophosphoryl trichloride in the presence of a catalyst under special conditions.

2. Description of the Prior Art

Phenylphosphonothioic dichloride (PPTC) is a common intermediate for the production of insecticides and flame-proofing agents. It has been disclosed to produce PPTC by reacting benzene with phosphorus trichloride in the presence of aluminum trichloride to form a complex and then vulcanizing the complex (Japanese Patent Publication No. 2669/1956). In accordance with this method, equimolar amounts of aluminum trichloride and product PPTC are required. Furthermore, this method is complicated, especially as regards the treatment of aluminum chloride waste. Additionally, the method has significant industrial disadvantages due to the high cost of aluminum trichloride in the production of PPTC. It has also been known to produce PPTC by reacting benzene with phosphorus trichloride using thermal decomposition to form phenylphosphonous dichloride and then vulcanizing the product. In this method, since thermal decomposition at high temperature is required, a reactor made of anticorrosive material is necessary. Accordingly, it is a disadvantageous method.

On the other hand, it has also been disclosed to produce PPTC by reacting benzene with thiophosphoryl trichloride in an autoclave at 200° – 450° C in Japanese Patent Application Disclosure No. 86823/1973. In accordance with this method, the reaction is quite slow at about 200° C and it has been necessary to heat the reactants to a temperature higher than 350° C for effective reaction. Consequently, a reactor made of anticorrosive material having high compressive strength has been required for this process also. As a result, this method also has disadvantages for industrial operation. Finally, it has been disclosed that PPTC can be produced by refluxing benzene with thiophosphoryl trichloride in the presence of a Friedel-Crafts catalyst. In accordance with this method, a large amount of diphenylphosphonothioic monochloride by-product has been produced and about 12 - 15 hours of reaction time has been required. Accordingly, it also possesses significant industrial disadvantages. Consequently, it would be most desirable to have a process for preparation of PPTC which is very attractive industrially.

SUMMARY OF THE INVENTION

Accordingly, it is an object of this invention to provide a process for industrially producing phenylphosphonothioic dichloride in high yield by reacting benzene with thiophosphoryl trichloride.

It is another object of this invention to provide a process for producing phenylphosphonothioic dichloride with little by-product.

It is still another object of this invention to provide a process for producing phenylphosphonothioic dichloride using a relatively short reaction time at relatively low temperature under relatively low pressure.

These and other objects of the present invention, as will hereinafter be made clear by the ensuing discussion, have been attained by providing a process for producing phenylphosphonothioic dichloride by reacting benzene with thiophosphoryl trichloride in the presence of a catalyst selected from the group consisting of Al, $AlCl_3$ —$P_2S_5$—$PCl_3$, $AlCl_3$—$P_2S_5$, $AlCl_3$—$PCl_3$ and $AlCl_3$, under a self-generated pressure of higher than 5 atm. at 100° – 300° C.

DETAILED DESCRIPTION OF THE PREFERRED EMBODIMENTS

The reaction of this invention is shown as follows:

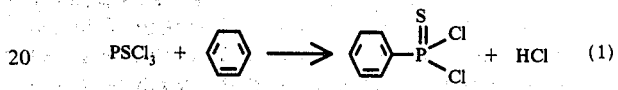

A key feature of this invention involves conducting the reaction in the presence of the catalyst under self-generated pressure, which is caused mainly by hydrogen chloride gas generated by the reaction. The self-generated pressure includes the pressure maintained during the discharging of portions of the hydrogen chloride gas from the closed autoclave. However, the pressure is not produced by compression.

In the process of this invention, benzene, thiophosphoryl trichloride and the catalyst are charged into an autoclave and the autoclave is heated while stirring the mixture under the self-generated pressure. In the reaction, the molar ratio of thiophosphoryl trichloride to benzene should be in the range of 0.1/1 –20/1, preferably 1/1 – 5/1, especially 1/1 – 2/1. That is, an equimolar or excess amount of thiophosphoryl trichloride to benzene is preferably used. The unreacted thiophosphoryl trichloride can be recovered and reused.

The suitable types of catalysts are Al, $AlCl_3$ —$P_2S_5$—$PCl_3$, $AlCl_3$—$P_2S_5$, $AlCl_3$—$PCl_3$ and $AlCl_3$. The combination of $AlCl_3$ and $P_2S_5$, especially the combination of $AlCl_3$, $P_2S_5$ and $PCl_3$ impart remarkably superior effects under the self-generated pressure. When metallic aluminum is used as the catalyst, the reaction mixture produced by reacting the metallic aluminum with thiophosphoryl trichloride includes a catalyst which may be similar to the combination of $AlCl_3$, $P_2S_5$ and $PCl_3$. When the catalyst is $AlCl_3$, the effect of the invention is relatively lessened compared to the other cases. The amount of catalyst required is remarkably less than that for the Friedel-Crafts catalyst and is usually 0.01 to 0.2 mole of $AlCl_3$ to one mole of benzene, preferably 0.03 – 0.15 mole, especially 0.05 – 0.1 mole. The molar ratio of $P_2S_5$ or $PCl_3$ to $AlCl_3$ in the combination catalysts is not critical but is usually 0.1 to 10, preferably 0.2 to 5. It is especially preferable to use a catalyst combination of $AlCl_3$ and 0.2 – 5 molar percent $P_2S_5$ and/or 0.2 – 5 molar percent $PCl_3$.

The reaction temperature should be in a range of 100° – 300° C, preferably 150° – 280° C, especially 180° – 250° C. The required reaction time is relatively long at a temperature less than 150° C, and the formation of by-products is a problem at a temperature higher than 280° C. The self-generated pressure is usually higher than 5 Kg/cm², preferably higher than 10 Kg/cm², and is maintained by the pressure of hydrogen chloride gas. When hydrogen chloride gas is discharged to maintain a pressure lower than 10 Kg/cm², the formation of the by-product of diphenylphosphonothioic monochloride is increased and the yield of PPTC is correspondingly decreased. The level of the self-generated pressure in the closed autoclave is dependent upon the size of the autoclave and the amount of the starting material available to generate hydrogen chloride gas. The pressure can be controlled by discharging a part of the hydrogen chloride gas, although it is preferred to control the amount of the starting material employed to that amount which yields the desired self-generated pressure without requiring discharge. The reaction time should be in the range of 0.5 to 20 hours, preferably less than 20 hours, most preferably less than 10 hours. Under the optimum conditions, PPTC can be produced in high yields in 1 – 2 hours. After the reaction, if necessary, the autoclave is cooled and hydrogen chloride gas in the autoclave is removed to obtain the reaction product. The reaction product can be analyzed by gas chromatography to determine the yield of PPTC, the by-products of diphenylphosphonothioic monochloride and triphenylphosphinesulfide, unreacted thiophosphoryl trichloride and unreacted benzene. The object product of PPTC can be easily recovered without substantial loss by distillation under reduced pressure. The yield of PPTC is usually 74–79% when metallic aluminum or $AlCl_3$—$P_2S_5$—$PCl_3$ is employed and 68–75% in the case of $AlCl_3$—$P_2S_5$. When $AlCl_3$ alone is used as the catalyst, the yield is relatively lower, but can be as high as 60 – 67%.

In accordance with this invention, the formation of by-products is remarkably low and the object product, PPTC, can be produced at relatively low temperature in high yields in a short time. Accordingly, industrial production of PPTC can be effectively performed.

Having generally described the invention, a more complete understanding can be obtained by reference to certain specific Examples, which are provided herein for purposes of illustration only and are not intended to be limiting unless otherwise specified. In the Examples, the by-product of diphenylphosphonothioic monochloride is referred to as DPPTC and the by-product of triphenylphosphinesulfide is referred to as TPPS. The self-generated pressure is shown as the pressure of the autoclave at the final stage of the reaction.

EXAMPLE 1

Al

In a 100 cc autoclave, 42.35 g (0.25 mole) of thiophosphoryl trichloride, 19.53 g (0.25 mole) of benzene and 0.5 g of metallic aluminum powder were charged and the reaction was conducted with stirring at 180° C for 4 hours under the self-generated pressure of hydrogen chloride gas. After cooling to room temperature, the valve of the autoclave was opened to discharge hydrogen chloride gas into a collector filled with an alkaline solution. The reaction product was transferred to a flask and was distilled under a reduced pressure to obtain 39.6 g of the liquid product which had a refractive index of $N_D^{25}$ 1.6222 and a boiling point of 115° C/5 mm Hg. The yield was 75%.

EXAMPLE 2

Al

In a 100 cc autoclave, 84.7 g (0.5 mole) of thiophosphoryl trichloride, 19.53 g (0.25 mole) of benzene and 0.5 g of metallic aluminum powder were charged, and the reaction was conducted with stirring at 200° C for 4 hours under the self-generated pressure of hydrogen chloride. (60 Kg/cm² of pressure at the final stage). The reaction mixture was treated in accordance with the process of Example 1 to obtain 42.0 g of the liquid product having the same refractive index and boiling point. The yield was 79%.

REFERENCE EXAMPLE 1

In a 100 cc autoclave, 42.35 g (0.25 mole) of thiophosphoryl trichloride, 19.53 g (0.25 mole) of benzene were charged, and the mixture was heated with stirring at 200° C for 4 hours. The reaction mixture was treated in accordance with the process of Example 1. No phenylphosphonothioic dichloride was produced.

EXAMPLE 3

$AlCl_3$

In a 300 cc autoclave, 167 g (0.986 mole) of thiophosphoryl trichloride, 58.5 g (0.75 mole) of benzene and 7.4 g (0.0556 mole) of $AlCl_3$ were charged, and the reaction was conducted with stirring at 190° C for 2 hours under the self-generated pressure of hydrogen chloride gas. (52 Kg/cm² of pressure at the final stage.) After cooling to room temperature, the valve of the autoclave was opened to discharge hydrogen chloride gas into a collector filled with an alkaline solution to obtain 207.5 g of the reaction product. A part of the reaction product was sampled and was analyzed by gas chromatography. (apparatus: Shimazu GC-6 APT; glass column: length of 1 m, inner diameter of 3 mm; column temperature: 60°–300° C, 20° C/min.; filler: silicon gum SE-30, 10 wt. % support of 60-80 mesh; carrier gas: helium, 40 ml/min. atm.; inlet pressure: 0.7 Kg.G/cm²; detector temperature: 300° C; and standard material: n-decane). The reaction product contained the following components:

| | |
|---|---|
| PPTC | 98.0 g (0.464 mole) |
| DPPTC | 7.5 g (0.0297 mole) |
| TPPS | 1.1 g (0.0037 mole) |
| unreacted $PSCl_3$ | 48.0 g |
| unreacted benzene | 6.0 g |

The yield of PPTC (relative to benzene) was 62.0 %.

EXAMPLE 4

$AlCl_3$

The process of Example 3 was repeated except for use of 3.7 g (0.0278 mole) of $AlCl_3$ and reaction at 250° C, to obtain 204 g of the reaction product which contained the following components (59 Kg/cm² of pressure at the final stage):

| | |
|---|---|
| PPTC | 106.0 g (0.502 mole) |
| DPPTC | 5.0 g (0.0198 mole) |
| TPPS | 1.2 g (0.0041 mole) |
| unreacted $PSCl_3$ | 45.0 g |

| | |
|---|---|
| unreacted benzene | 3.0 g |

The yield of PPTC (relative to benzene) was 67.0 %.

EXAMPLE 5

AlCl₃

The process of Example 3 was repeated except for use of 10.0 g (0.075 mole) of AlCl₃ and reaction at 170° C for 8 hours to obtain 212 g of the reaction product which contained the following components: (40 Kg/cm² of pressure at the final stage)

| | |
|---|---|
| PPTC | 95.0 g (0.450 mole) |
| DPPTC | 9.5 g (0.0376 mole) |
| TPPS | 0.5 g (0.0017 mole) |
| unreacted PSCl₃ | 50.0 g |
| unreacted benzene | 7.0 g |

The yield of PPTC (relative to benzene) was 60 %.

COMPARATIVE EXPERIMENT 1

The process of Example 3 was repeated except for reaction under the pressures of 5,10 and 50 Kg/cm² maintained by discharging hydrogen chloride gas from the valve of the autoclave. The reaction products contained the following components which are shown in yields relative to benzene.

| Yields of components in the reaction products | | | |
|---|---|---|---|
| Component | 5 Kg/cm² | 10 Kg/cm² | 50 Kg/cm² |
| PPTC | 28 % | 58 % | 62 % |
| DPPTC | 20 % | 8 % | 4 % |
| TPPS | 5 % | 3 % | 0.2 % |

The yield was determined by the equation:

$$\text{Yield of each component (\%)} = \frac{\text{each component (mole)}}{\text{benzene (mole)}} \times 100.$$

REFERENCE EXAMPLE 2

The process of Example 3 was repeated except for using no AlCl₃ catalyst and reacting for 4 hours at 190°, 250° and 300° C. The yields of PPTC under said conditions were as follows.

| | Yield of PPTC | | |
|---|---|---|---|
| Reaction temperature | 190° C | 250° C | 300° C |
| Yield of PPTC | 0 % | 0 % | 2 % |

EXAMPLE 6

AlCl₃ — PCl₃

The process of Example 3 was repeated except using 7.4 g (0.0556 mole) of AlCl₃ and 11.4 g (0.0833 mole) of PCl₃ as the catalyst. The reaction product contained the following components (53 Kg/cm² of pressure at the final stage):

| | |
|---|---|
| PPTC | 103 g (0.488 mole) |
| DPPTC | 6.3 g (0.0250 mole) |
| TPPS | 0.7 g (0.0024 mole) |
| unreacted PSCl₃ | 49 g |
| unreacted benzene | 5.2 g |

The yield of PPTC relative to benzene was 65 %.

COMPARATIVE EXPERIMENT 2

The process of Example 6 was repeated except that the reaction was conducted under the pressures of 5, 10 and 50 Kg/cm² maintained by discharging hydrogen chloride gas from the valve of the autoclave. The reaction products contained the following components which are shown in yields relative to benzene.

| Yields of components in the reaction products | | | |
|---|---|---|---|
| Component | 5 Kg/cm² | 10 Kg/cm² | 50 Kg/cm² |
| PPTC | 30 % | 60 % | 65 % |
| DPPTC | 20 % | 6.3 % | 3.3 % |
| TPPS | 4.6 % | 2.2 % | 0.3 % |

EXAMPLE 7

AlCl₃ - P₂S₅

The process of Example 3 was repeated except using 7.4 g (0.0556 mole) of AlCl₃ and 6.2 g of P₂S₅ as the catalyst to obtain 214.5 g of the reaction product (55 Kg/cm² of pressure at the final stage). The reaction product contained the following components:

| | |
|---|---|
| PPTC | 114.0 g (0.540 mole) |
| DPPTC | 6.4 g (0.0253 mole) |
| TPPS | 1.3 g (0.0044 mole) |
| unreacted PSCl₃ | 48.0 g |
| unreacted benzene | 5.4 g |

The yield of PPTC relative to benzene was 72 %.

EXAMPLE 8

AlCl₃ - P₂S₅

The process of Example 7 was repeated except using 3.7 g (0.0278 mole) of AlCl₃ and 6.2 g (0.0278 mole) of P₂S₅ as the catalyst and reacting at 230° C for 2 hours, to obtain 209 g of the reaction product. The reaction product contained the following components (62 Kg/cm² of pressure at the final stage):

| | |
|---|---|
| PPTC | 118.0 g (0.560 mole) |
| DPPTC | 5.2 g (0.0206 mole) |
| TPPS | 1.0 g (0.0034 mole) |
| unreacted PSCl₃ | 47.0 g |
| unreacted benzene | 3.0 g |

The yield of PPTC relative to benzene was 75 %.

EXAMPLE 9

AlCl₃ — P₂S₅

The process of Example 7 was repeated except using 10.0 g (0.075 mole) of AlCl₃, and 6.2 g (0.0278 mole) of P₂S₅ as the catalyst and reacting at 150° C for 8 hours, to obtain 217 g of the reaction product. The reaction product contained the following components (43 Kg/cm² of pressure at the final stage):

| | |
|---|---|
| PPTC | 107.0 g (0.506 mole) |
| DPPTC | 9.8 g (0.0388 mole) |
| TPPS | 0.8 g (0.0027 mole) |
| unreacted PSCl₃ | 46.0 g |
| unreacted benzene | 5.0 g |

The yield of PPTC relative to benzene was 68 %.

COMPARATIVE EXPERIMENT 3

The process of Example 7 was repeated except reacting under the pressures of 5, 10 and 50 Kg/cm² maintained by discharging hydrogen chloride gas from the valve of the autoclave. The reaction products contained the following components which are shown in yields relative to benzene.

| Yields of components in the reaction products | | | |
|---|---|---|---|
| Component | 5 Kg/cm² | 10 Kg/cm² | 50 Kg/cm² |
| PPTC | 32 % | 68 % | 72 % |
| DPPTC | 20 % | 5.2 % | 3.5 % |
| TPPS | 4.3 % | 2.1 % | 0.6 % |

EXAMPLE 10

$AlCl_3 - P_2S_5 - PCl_3$

In a 300 cc autoclave, 167 g (0.986 mole) of thiophosphoryl trichloride, 58.5 g (0.75 mole) of benzene and 7.4 g (0.0556 mole) of AlCl₃, 6.2 g (0.0278 mole) of P₂S₅ and 11.4 g (0.0833 mole) of PCl₃ were charged and the reaction was conducted with stirring at 190° C for 2 hours under the self-generated pressure of hydrogen chloride gas. After cooling to room temperature, the valve of the autoclave was opened to discharge hydrogen chloride gas into a collector filled with an alkaline solution to obtain 225.5 g of the reaction product. The reaction product contained the following components (58 Kg/cm² of pressure at the final stage):

| | |
|---|---|
| PPTC | 122 g (0.576 mole) |
| DPPTC | 8 g (0.0317 mole) |
| TPPS | 0 g (0) |
| unreacted PSCl₃ | 54 g |
| unreacted benzene | 3 g |

The yield of PPTC relative to benzene was 77 %.

EXAMPLES 11-13

$AlCl_3 - P_2S_5 - PCl_3$

The process of Example 10 was repeated except varying the amounts of AlCl₃, P₂S₅ and PCl₃ used in the catalyst. The yields of PPTC relative to benzene are as follows:

| | AlCl₃ | P₂S₅ | PCl₃ | Yield |
|---|---|---|---|---|
| Example 10 | 7.4 g (0.0556 mole) | 6.2 g (0.0278 mole) | 11.4 g (0.0833 mole) | 77 % |
| Example 11 | 7.4 g | 6.2 g | 22.8 g | 76 % |
| Example 12 | 7.4 g | 3.1 g | 11.4 g | 77 % |
| Example 13 | 7.4 g | 12.4 g | 11.4 g | 74 % |

EXAMPLE 14

$AlCl_3 - P_2S_5 - PCl_3$

The process of Example 10 was repeated except using 3.7 g (0.0278 mole) of AlCl₃, 6.2 g (0.0278) of P₂S₅ and 11.4 g (0.0833 mole) of PCl₃, and reacting at 225° C for 2 hours to obtain 223 g of the reaction product. The reaction product contained the following components (63 Kg/cm² of pressure at the final stage):

| | |
|---|---|
| PPTC | 125 g (0.592 mole) |
| DPPTC | 4.5 g (0.0178 mole) |
| TPPS | 1.0 g (0.0034 mole) |
| unreacted PSCl₃ | 53 g |
| unreacted benzene | 4 g |

The yield of PPTC relative to benzene was 79%.

EXAMPLE 15

$AlCl_3 - P_2S_5 - PCl_3$

The process of Example 10 was repeated except using 10.0 g (0.075 mole) of AlCl₃, 6.2 g (0.0278) of P₂S₅ and 11.4 g (0.0833 mole) of PCl₃, and reacting at 150° C for 8 hours to obtain 228 g of the reaction product. The reaction product contained the following components (47 Kg/cm² of pressure at the final stage):

| | |
|---|---|
| PPTC | 118 g (0.559 mole) |
| DPPTC | 9 g (0.0357 mole) |
| TPPS | 0.8 g (0.0027 mole) |
| unreacted PSCl₃ | 54 g |
| unreacted benzene | 4 g |

The yield of PPTC relative to benzene was 75 %.

COMPARATIVE EXPERIMENT 4

The process of Example 10 was repeated except for reaction under the pressures of 5, 10 and 50 Kg/cm² maintained by discharging hydrogen chloride gas from the valve of the autoclave. The reaction products contained the following components which are shown in yields relative to benzene.

| Yields of components in the reaction products | | | |
|---|---|---|---|
| Component | 5 Kg/cm² | 10 Kg/cm² | 50 Kg/cm² |
| PPTC | 33 % | 74 % | 77 % |
| DPPTC | 22 % | 4.5 % | 3.5 % |
| TPPS | 3 % | 2 % | 0.7 % |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for producing phenylphosphonothioic dichloride by reacting benzene with thiophosphoryl trichloride, the improvement characterized in that the reaction is conducted in the presence of a catalyst selected from the group consisting of Al, $AlCl_3$, a combination of $AlCl_3$, $P_2S_5$ and $PCl_3$, a combination of $AlCl_3$ and $P_2S_5$, and a combination of $AlCl_3$ and $PCl_3$, under the self-generated pressure of hydrogen chloride gas at a temperature of 100°–300° C.

2. The process of claim 1, wherein the self-generated pressure of hydrogen chloride gas is higher than 10 $Kg/cm^2$ maintained by discharging a part of the hydrogen chloride gas from the autoclave.

3. The process of claim 1, wherein the catalyst is selected from the group consisting of a combination of $AlCl_3$, $P_2S_5$ and $PCl_3$, a combination of $AlCl_3$ and $P_2S_5$ and a combination of $AlCl_3$ and $PCl_3$.

4. The process of claim 1, wherein the catalyst is Al.

5. The process of claim 1, wherein the catalyst is $AlCl_3$.

6. The process of claim 1, wherein the reaction temperature is in the range of 150° – 280° C, and the self-generated pressure of hydrogen chloride gas is higher than 10 $Kg/cm^2$.

7. The process of claim 1, wherein the molar ratio of thiophosphoryl trichloride to benzene is 0.1/1 to 20/1.

8. The process of claim 1, wherein the molar ratio of the amount of catalyst to that of benzene is 0.01 to 0.2.

9. The process of claim 1, wherein the molar ratio of each additive in the combination catalysts to $AlCl_3$ is 0.1 to 10.

* * * * *